United States Patent [19]
Chalana et al.

[11] Patent Number: 5,605,155
[45] Date of Patent: Feb. 25, 1997

[54] ULTRASOUND SYSTEM FOR AUTOMATICALLY MEASURING FETAL HEAD SIZE

[75] Inventors: Vikram Chalana, Mountlake Terrace; Yongmin Kim; David R. Haynor, both of Seattle, all of Wash.

[73] Assignee: University of Washington, Seattle, Wash.

[21] Appl. No.: 624,949

[22] Filed: Mar. 29, 1996

[51] Int. Cl.$^6$ .................................................. A61B 8/00
[52] U.S. Cl. .............................. 128/660.07; 128/661.05
[58] Field of Search ..................... 128/660.01, 660.09, 128/660.07, 661.05, 661.09, 661.1; 364/413.13, 413.25; 382/128

[56] References Cited

U.S. PATENT DOCUMENTS

| | | | |
|---|---|---|---|
| 5,107,838 | 4/1992 | Yamaguchi | 128/653.2 |
| 5,360,006 | 11/1994 | Geiser et al. | 128/653.1 |
| 5,457,754 | 10/1995 | Han et al. | 382/128 |
| 5,465,721 | 11/1995 | Kishimoto et al. | 128/660.07 |
| 5,469,850 | 11/1995 | Iizuha et al. | 128/660.07 |
| 5,492,125 | 2/1996 | Kim et al. | 128/660.07 |

OTHER PUBLICATIONS

Matsopoulos, G. K. et al., "Use of Morphological Image Processing Techniques for the Measurement of a Fetal head from Ultrasound Images," Pattern Recognition, vol. 27, No. 10; 1994.

Lee et al., "MediaStation 5000: An Integrated Multimedia Video and Audio Processing System".

Primary Examiner—Francis Jaworski
Attorney, Agent, or Firm—Koda Law Office

[57] ABSTRACT

An ultrasound system automatically measures fetal head size from ultrasound images. An ultrasound image of the fetal head is detected. A radial maxima point is identified on each of a plurality of radii extending from a substantially common vertex point within the fetal head image. Each radial maxima point corresponds to an ultrasound sample along its corresponding radius, and has a maximum ultrasound echo strength. A first curve is defined from the radial maxima points. The remaining unfiltered radial maxima points are fit to a second curve, and the second curve is the detected curved boundary. The detected curve boundary is modified to define an initial fetal head boundary. An inner fetal head boundary and outer fetal head boundary are derived from the initial fetal head boundary and a predetermined fetal skull thickness, and fetal head size is computed from the inner fetal head boundary and the outer fetal head boundary.

20 Claims, 9 Drawing Sheets

ULTRASOUND SYSTEM FOR AUTOMATICALLY MEASURING FETAL HEAD SIZE

BACKGROUND OF THE INVENTION

This invention relates to image processing methods used in ultrasound medical diagnostic imaging systems. More particularly, this invention relates to a method for automatically measuring fetal head size from ultrasound image data.

Ultrasound medical diagnostic systems generate images of anatomical structures within a patient's body by scanning a target area with ultrasound signals. Typically, ultrasound signals on the order of 2.0 MHz to 10 MHz are transmitted into a patient via a transducer probe. The transmitted ultrasound energy is in part absorbed, dispersed, refracted, and reflected by the patient's body. Reflected ultrasound energy is received at the transducer probe where it is converted into electronic echo signals. The echo signals undergo beam-forming to correlate the ultrasound signals. Subsequently the beam-formed signals are processed to analyze echo, doppler, and flow information and to obtain an image of the patient's targeted anatomy (e.g., tissue, flow, doppler).

A B-mode image, for example, is a brightness image in which component pixels are brightened in proportion to a corresponding echo signal strength. The brightness image represents a cross section of a patient target area through a transducer's scanning plane. Typically the B-mode image is a gray scale image in which the range of darker to lighter gray-scale shades corresponds to increasing brightness or echo strength.

One common ultrasound application is to view a fetus within the mother's womb during a prenatal care stage. It is desirable to view the fetus to diagnose its health, sex, and age. Fetal head measurements, the subject of this invention, are useful for evaluating fetal growth, estimating fetal weight, predicting intra-uterine growth retardation and fetal maturity, and estimating gestational age. The fetal head measurements of interest include fetal head circumference ("HC") and fetal biparietal diameter ("BPD"). The biparietal diameter is the distance between the two parietal bones of the skull at points just above the ears.

Conventionally, these measurements have been performed manually by a sonographer. Head circumference is measured by plotting minor and major ellipse axes on the image, then calculating circumference based upon such axial distances. Thus, the fetal head head is assumed to be an ellipse. The ellipse circumference serves as an estimate of the fetal head circumference. Biparietal diameter is measured using a caliper to read the distance on the fetal ultrasound image. One shortcoming of this conventional manual measurement approach is that the time used in performing the measurements is a large portion of the overall fetal ultrasound scanning process time. Another shortcoming is that the manual measurements introduce operator inaccuracies which impact related and subsequent diagnoses. Some efforts to reduce the time requirement have added to the inaccuracies.

For example, by opening an ellipse to estimate head circumference an inaccuracy is introduced. Specifically, because the head is not likely to be a perfect ellipse, the circumference has a degree of inaccuracy. Because the head circumference is used to derive other parameters and values, there is a degree of inaccuracy throughout the diagnostic evaluation. Even more problematic is that the inaccuracy is not consistent. Different operators may introduce different degrees of inaccuracy. Thus, it is difficult to obtain a meaningful profile of statistics for a given population of data. For example, growth curves used for aging the fetus have been derived from data having varying degrees of inaccuracies decreasing the reliability of the diagnosed age. Reliability of other estimates such as computation of head-to-abdominal circumference ratios and estimation of fetal weight also is reduced. An error in estimating biparietal diameter by about 0.8 mm results, for example, changes estimated gestational age by about one-half week. An error in estimating head circumference by about 7 mm changes estimated gestational age by about one full week. Variability of fetal head size measurements among different operators often ranges between 2% and 7%. As a result, estimated gestational age derived from manual measurements of different sonographers have varied by more than one week. Accordingly, there is a need for a more accurate, more consistent method for measuring fetal head size.

SUMMARY OF THE INVENTION

According to the invention, fetal head size, as displayed in an ultrasound medical diagnostic imaging system, is automatically measured. An operator positions an ultrasound transducer probe on a mother's abdomen to display the Fetus within the womb. The operator manipulates the probe to image the fetal head at a desired orientation. Specifically, the probe is oriented to capture a cross-section of the fetal head along a longitudinal axis (e.g., from the top of the head downward.) The cross-section is captured as a snap-shot and displayed as a two dimensional ("2D") ultrasound image. The operator then sets a marker at the approximate center of the fetal head. Fetal head size then is automatically derived from the ultrasound data and the marked position.

According to one aspect of the invention, at one step radial samples of a filtered gradient of the image are taken to define radial maxima points. Such radial samples are based from the marker extending outward to a brightened maxima point (i.e., strongest endpoint of the radial line). Such maxima points are expected to represent a crude boundary of the fetal skull. According to one embodiment more than 100 radial samples are taken to define the radial maxima points. Because some points along the true fetal skull may not have been captured during the ultrasound scan, some of the radial maxima points may occur at an exaggerated radial increment beyond the true fetal skull. These are referred to herein as outlier points. At a next step, a statistical filter is used to filter away the outlier points. In one embodiment all boundary points with a radial distance greater than two standard deviations from a mean are automatically removed. In addition, all boundary points that are asymmetric to other boundary points are removed by a symmetric filter. A curve is fit through the filtered crude boundary. In one embodiment, a cubic spline is fit through the points of the filtered crude boundary. The filtered crude boundary, fit with a curve, is the initial boundary estimate of the fetal head.

According to another aspect of the invention, the initial boundary is adjusted to derive a boundary which lies between the inner and outer boundaries of the fetal skull. At one step, a first contouring model is applied to the initial boundary. According to an aspect of the invention, contour model parameters are automatically estimated. The contouring process is an iterative process of fitting the initial boundary and ultrasound data to a contour model. Once the iterations achieve less than a threshold improvement over a prior iteration (e.g., when the model parameters and the boundary stop changing), the iterative process ceases. The result is an improved boundary estimate which lies between the inner and outer boundaries of the fetal skull.

According to another aspect of the invention, at another step inner and outer boundaries of the fetal skull are derived from the improved boundary. The improved boundary is expanded using a second contouring model to find an outer boundary, and contracted using a third contouring model to find an inner boundary. A universal average fetal skull thickness is used to define expansion and contraction factors. Such expansion and contraction factors along with the improved boundary define initial curves for the second and third contouring models. Iterative fitting processes then are performed to derive the outer fetal skull boundary and the inner fetal skull boundary.

According to another aspect of the invention, at another step fetal head size is automatically computed from the inner and outer boundaries of the fetal head. Fetal head circumference is measured by automatically fitting an ellipse to the outer boundary, then calculating the circumference of such ellipse. Biparietal diameter is measured by fitting an ellipse to each of the outer and inner boundaries, then calculating the average length of the inner ellipse's minor axis and the outer ellipse's minor axis.

According to one advantage of the invention, the automatic measuring process reduces the portion of diagnostic scanning time allocated for measuring fetal head size. According to another advantage of the invention, the automatic measuring process reduces interoperator measurement deviations, thereby improving the reliability of such measurements as health and diagnostic indicators. The invention will be better understood by reference to the following detailed description taken in conjunction with the accompanying drawings.

DESCRIPTION OF SPECIFIC EMBODIMENTS

Exemplary Host Platform

Figure 1:
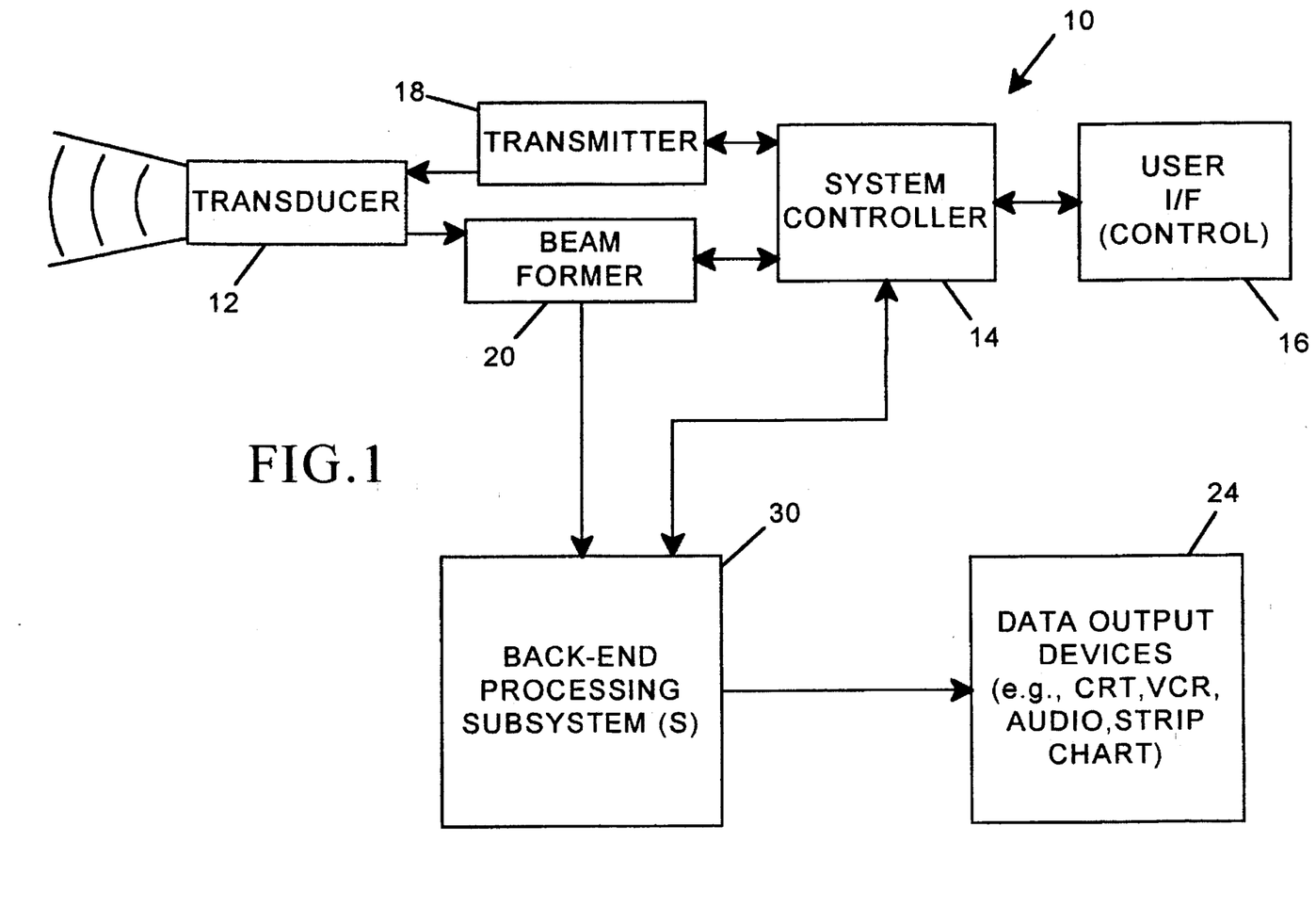
FIG. 1 is a block diagram of an ultrasound medical diagnostic imaging system.

FIG. 1 shows a block diagram of a host ultrasound medical diagnostic imaging system 10 for implementing a method embodiment of this invention. The function of the system 10 is to perform diagnostic imaging of a patient using ultrasound data. Ultrasound signals are transmitted via transducer 12 into a patient. In the case of a fetal ultrasound scan, the ultrasound signals are transmitted into the fetus. Reflected signals are detected and used to derive internal images of the patient, or fetus, for a scanned area/volume, such as a fetal head.

A system controller 14 receives and displays user control information via a user interface 16. During operation, system control signals are output to an ultrasound front end (i.e., transducer 12, a transmitter 18, a beam-former 20, and related circuitry) and to various subsystems. Transmitter 18 generates output signals to transducer 12 to define aperture, apodization, focus, and steering of ultrasound signals. Transducer 12 is an array of transducer elements. The elements define multiple channels, each channel for transmitting and/or receiving ultrasound signals. Transmitted ultrasound signals are in part absorbed, dispersed, refracted, and reflected when travelling through a patient or fetus. Reflected signals are sensed by transducer 12 and captured as a patterned beam by beam-former 20. The captured signals are sent to one or more back-end processing subsystems 30. The function of back-end processing subsystem(s) 30 is to process the raw beam data and generate image data for output devices 24.

Figure 2:
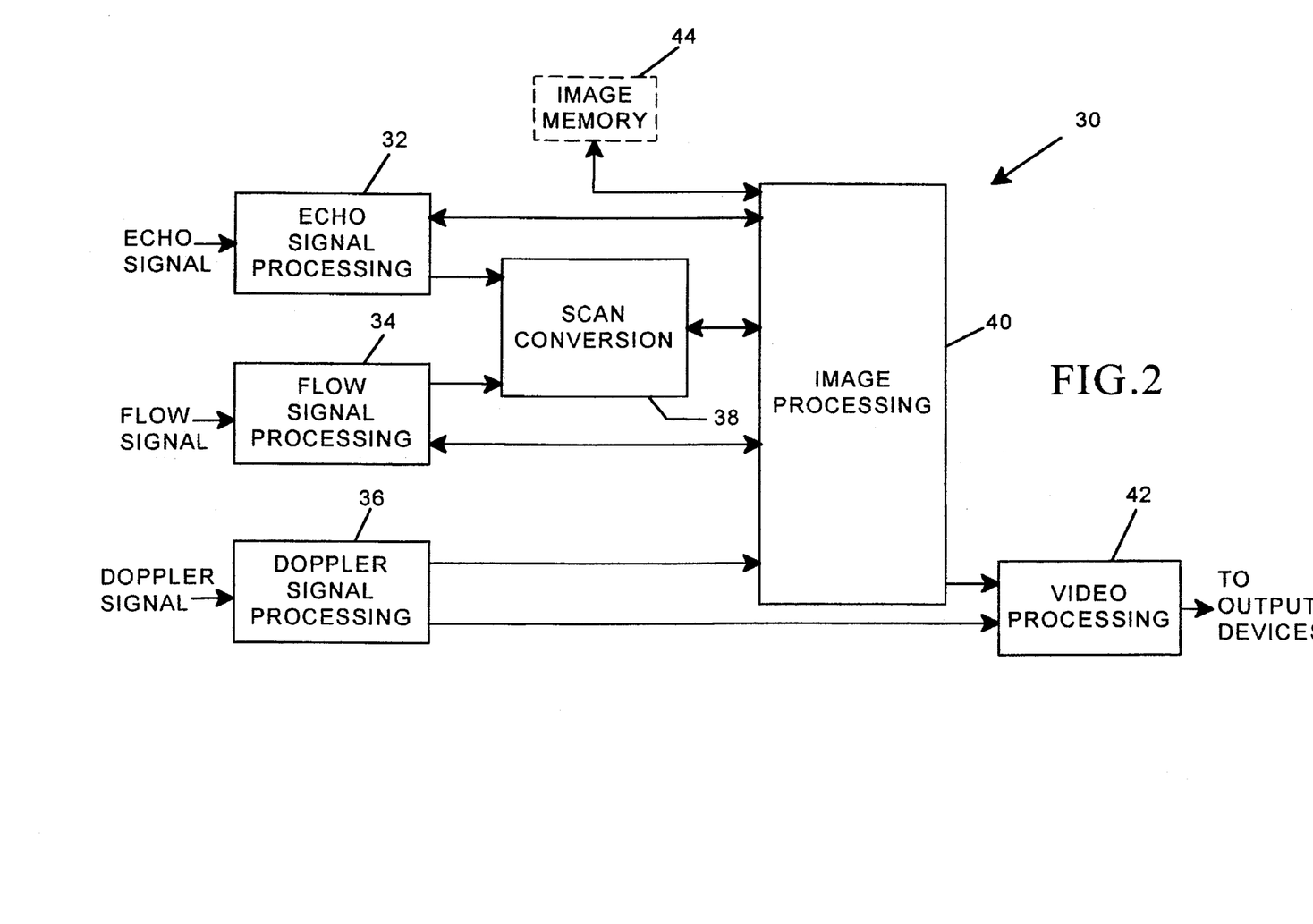
FIG. 2 is a block diagram of a preferred embodiment of back-end processing functions.

FIG. 2 is a block diagram of back-end processing functions. Digital echo signals, flow signals, and/or doppler signals are received at the back-end processing subsystem(s) 30 according to various modes of operation. Such input signals are referred to herein as vector signals. For a transducer 12 performing sector scanning, the vector signals are digital polar-coordinate data samples of echo, flow, and/or doppler signals. For a transducer 12 performing linear scanning, the vector signals are digital cartesian-coordinate data samples of echo, flow, and/or doppler signals.

Back-end processing includes echo signal processing 32, flow signal processing 34, doppler signal processing 36, scan conversion 38, image processing 40, and video processing 42. Echo signal processing 32 typically encompasses signal enhancement filtering, energy detection, and image enhancement filtering. Various filtering and convolution techniques are employed. The purpose of echo signal processing 32 is to enhance the signal-to-noise ratio of the echo signal. Flow signal processing 34 analyzes signals for flow parameters. Typical parameter derivations include sample correlation and flow averaging. The purpose of flow signal processing 34 is to identify flow and turbulence within a scanned area. Doppler signal processing 36 typically encompasses signal enhancement filtering, spectral estimation processing, energy detection, and derived waveform filtering. The purpose of doppler signal processing 36 is to identify and filter out doppler shift, to improve spectral frequency response and to coordinate spectral mapping.

A scan conversion process 38 converts the processed vector data streams from echo signal processing 32 and flow signal processing 34. For polar-coordinate vector data, the data is converted into cartesian-coordinate raster data. For cartesian-coordinate vector data, the data is scaled into cartesian-coordinate raster data.

Image processing 40 includes image enhancement and processing executed on the raster data or vector data. In an off-line delayed playback (e.g., cine playback) mode of operation image data, vector data and/or raster data is received from image memory 44 and processed. Preferably, image processing 40 performs image processing functions on the ultrasound images by applying the active contour model, as will be discussed in detail below. However, as will be appreciated, it is not necessary that image processing functions for applying the active contour model be performed within image processing 40.

Figure 3:
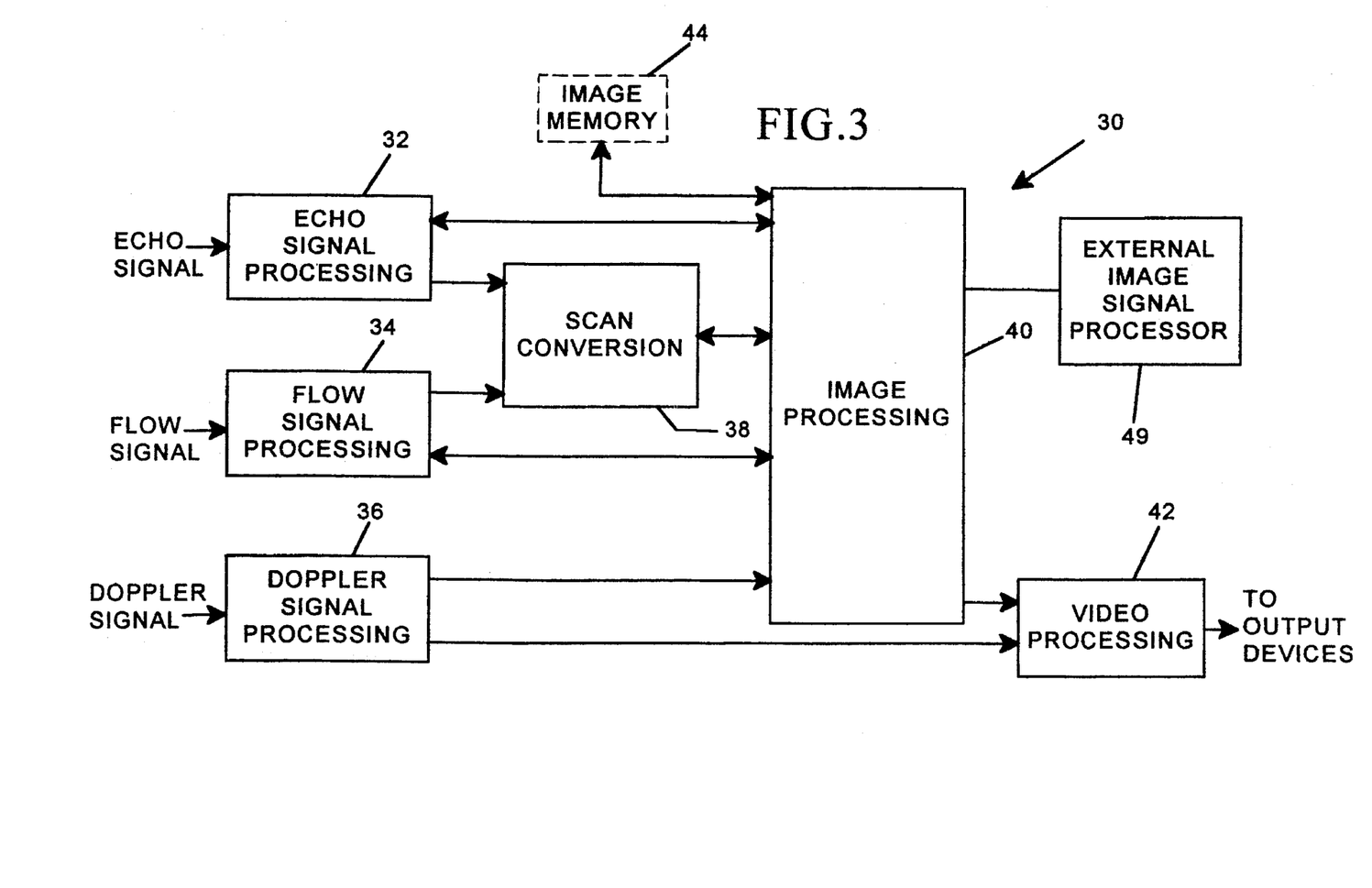
FIG. 3 is a block diagram of an alternate embodiment of back-end processing.

For example, FIG. 3 shows an alternate embodiment in which an external image signal processor 49 is connected to image processing 40. Image signal processors are well known in the art, and any one of a number of known processors may be acceptable. Accordingly, details of the construction and operation of external image signal processor 49 are omitted. An example of an acceptable signal processor is a Sun Sparcstation 20 workstation (Sun Microsystems, Mountain View, Calif.). In such an alternate embodiment, external image signal processor 49 performs the image processing functions according to the present invention. This alternate embodiment permits conventional ultrasound medical diagnostic imaging systems to automatically measure fetal head size according to the present invention without modification when coupled to external image processor 40.

Video processing 42 executes on the image processed data to generate video signals, audio signals, and graphing signals for output to a display device, audio device, storage device (e.g., VCR), and/or charting device. Video processing 42 in some applications also executes on doppler processed vector data to generate similar video signals, audio signals, and graphing signals for output to the display device, audio device, storage device, and/or charting device.

Method Overview

The method for automatically measuring fetal head size eliminates the need for the operator to estimate curve shapes and distances. Instead the operator need merely capture a 2D image of the fetal head at a desired orientation and set a marker at an approximate midpoint of the displayed image of the head. According to one embodiment of the invention, a filtered gradient of the image serves as a data sample set from which the fetal head measurements are derived.

First an initial boundary of the fetal head is estimated automatically using filtering techniques such as statistical filtering and symmetry filtering. The initial boundary is modified and improved to derive a boundary which lies between the inner and outer boundaries of the fetal skull using a first active contour model. Thereafter, inner and outer boundaries of the fetal skull are derived from the improved boundary using a second contouring model. Fetal head size then is automatically computed from the inner and outer boundaries of the fetal head. Following is a description of the active contour model used by the present invention and sections on specific embodiments for various steps of the inventive method.

Active Contour Model

The present invention uses an active contour model for finding inner and outer boundaries of the fetal skull. In applying such a model, the boundaries of the fetal head are represented as smooth, unbroken boundaries that lie along high gradient points (e.g., edges) in the fetal head image. For example, the contour passing over an image of the fetal head may be represented by v(s)=(x(s),y(s)), where x and y are the coordinates of the contour on the fetal head image, and s is a normalized contour length which defines parameters of the contour. The optimum contour representing the fetal head boundary is found by minimizing the following cost function:

$$E(v) = \int_0^1 \{\gamma d(v, \nabla I) + \alpha \|v_s\|^2 + \beta \|v_{ss}\|^2\} ds.$$

Here, I is the input fetal head image; $\nabla I$ is the gradient of the fetal head image I; $d(v, \nabla I)$ is a function that computes the extent to which the contour, v, passes through the "edges", or points of high gradient, in the fetal head image I; and $v_s$ and $v_{ss}$ are the first and second derivatives of the contour v with respect to the parameter s. The model parameters $\alpha$, $\beta$, and $\gamma$ control the relative importance of the three terms in finding the optimal contour on the fetal head image. Higher values of $\alpha$ and $\beta$ encourage shorter and smoother contours, respectively, while higher values of $\gamma$ encourage more irregular contours which follow edges of the fetal skull more closely. According to the present invention, the model parameters $\alpha$, $\beta$, and $\gamma$ are automatically estimated. This cost function is minimized by using an iterative gradient descent optimization method.

Deriving an Initial Fetal Head Boundary

Figure 4:
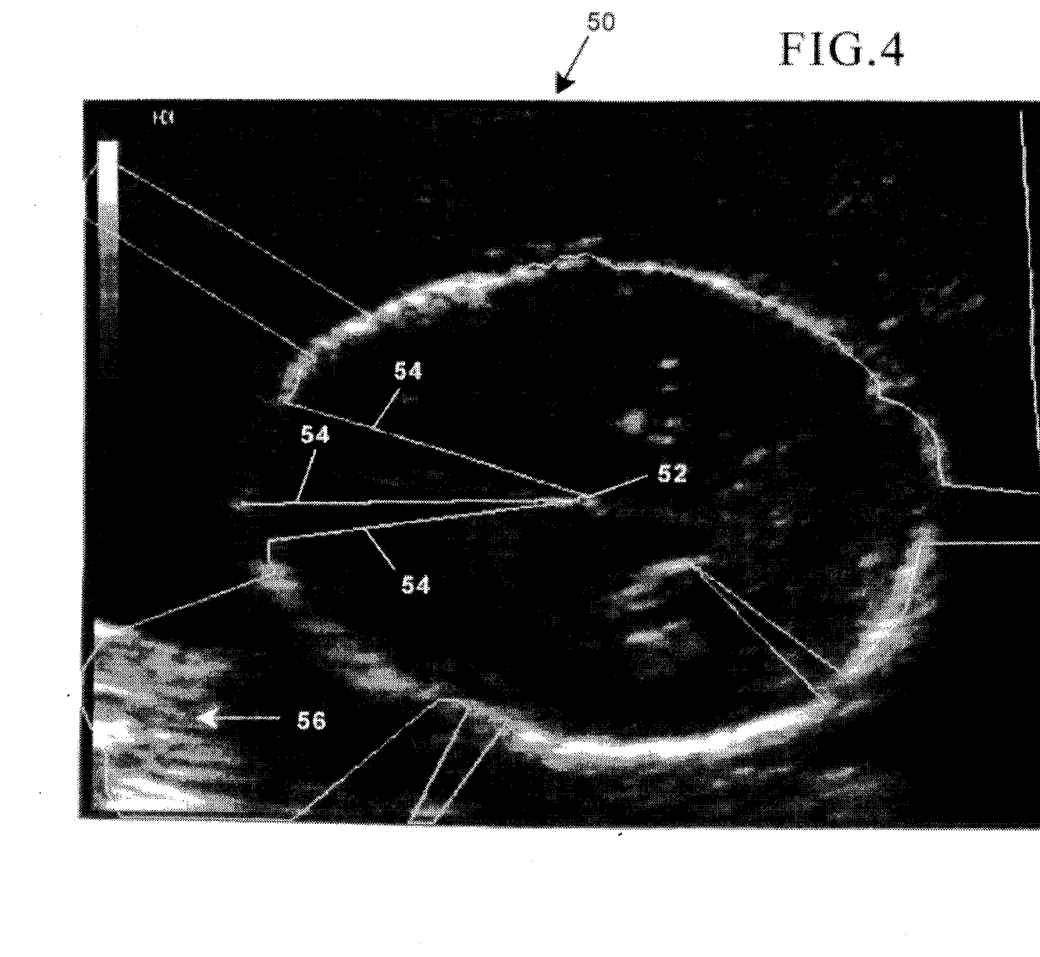
FIG. 4 is an ultrasound display image of a fetal head with overlaid scan lines at a first step of a fetal head measurement method according to one embodiment of the invention.

To apply the active contour model, first an initial contour on the fetal head image is chosen. Accordingly, the method of the present invention begins with a step of detecting a rough initial boundary of the fetal skull. Preferably, the initial contour is close to the displayed boundary of the fetal head. FIG. 4 shows a fetal head boundary detected in the first step in the method according to a preferred embodiment of the invention.

To detect the initial fetal skull boundary, the user locates a fetal head 50, using ultrasound images. The user positions an ultrasound transducer probe on a mother's abdomen to display the fetus within the womb. The operator manipulates the probe to image fetal head 50 at a desired orientation. Specifically, the probe is preferably oriented to capture a cross-section of fetal head 50 along a longitudinal axis (e.g., from the top of fetal head 50 downward.) The cross-section is captured as a snap-shot and is displayed as a two dimensional ("2D") ultrasound image on a display device such as a CRT. The operator then sets a marker at an initial point 52 that is near the approximate center of fetal head 50. Initial point 52 need not be marked exactly at the center of fetal head 50. Instead, according to the present invention, initial point 52 can be marked within a circle having a diameter of approximately 10 mm, and preferably a diameter of approximately 8 mm, from the true center of fetal head 50 without significant degradation of the resultant fetal head size.

According to the present invention, the above steps of detecting fetal head 50 and marking initial point 52 can be the only operator actions taken in measuring fetal head size. No further operator actions are necessary for the present invention to automatically measure fetal head size. However, further operator interaction may be desired to incorporate prior information known by the user about fetal head size parameters. These desired operator interventions can further refine the automatic measurements of fetal head size made according to the present invention; they are discussed later in the detailed description.

After the user detects fetal head 50 and marks initial point 52, the present invention automatically takes radial samples of a filtered gradient of the image of fetal head 50. Here, the image is preferably filtered by the derivative of a Gaussian gradient of the input image. According to the invention, the radial samples are taken to define radial maxima points. The radial samples are taken along radial lines 54 that extend outward from initial point 52 to maxima points (i.e., the points along radial lines 54 corresponding to a maximum ultrasound echo strength or image brightness). In one embodiment, the radial samples are the image gray values underlying the points that are one pixel distance apart from one another on the radial lines. The present invention determines the point of maximum gray value, representing the strongest edge, on each radial line 54. These maxima define a crude boundary of fetal head 50. The present invention may generate more than 100 radial lines 54, and preferably generates approximately 120 radial lines 54; when approximately 120 radial lines 54 are drawn, each radial line 54 is spaced approximately 3 degrees apart.

Some points along the true fetal skull may not have been captured during the ultrasound scan. Therefore, some of the radial maxima points may occur at an exaggerated radial increment beyond the true fetal skull. These points not lying on the true boundary of fetal head 50 are referred to herein as outlier points 56. As seen in FIG. 4, the crude boundary of fetal head 50 may include a number of outlier points 56. It is therefore desirable to remove outlier points 56 from the crude boundary.

Removing Outlier Points

Figure 5:
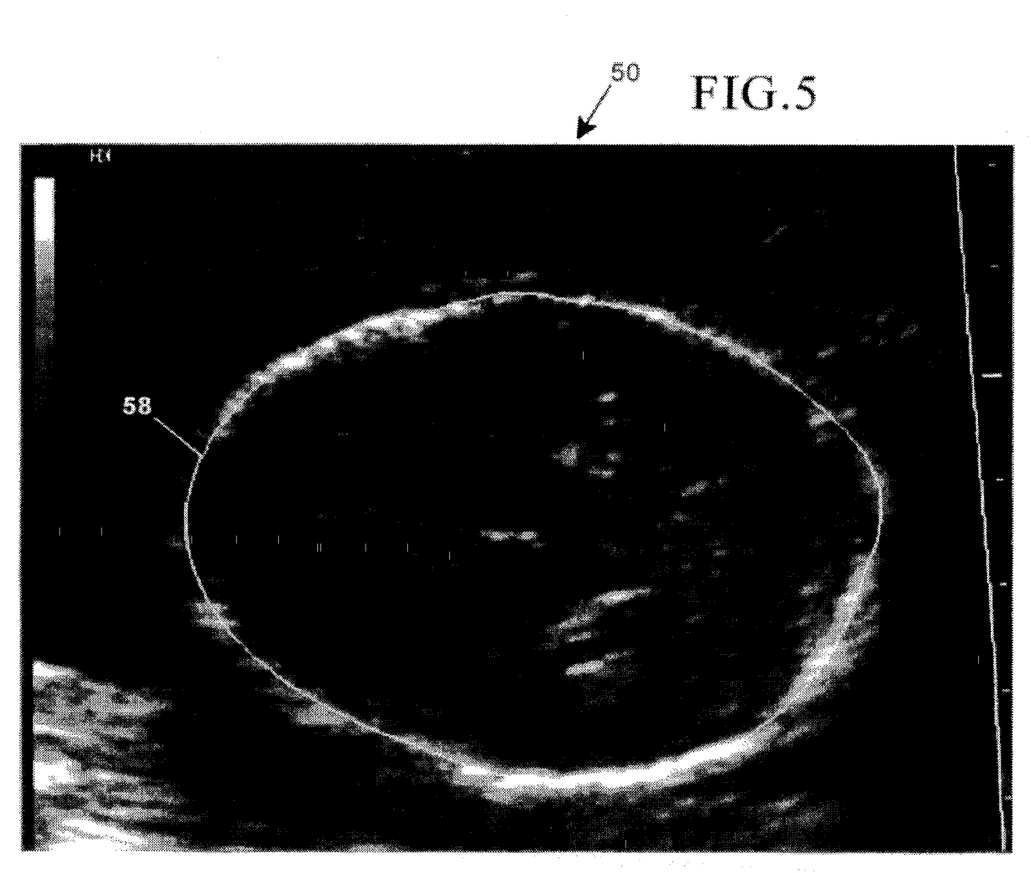
FIG. 5 is an ultrasound display image of a fetal head with an overlaid crude initial boundary at another step of a fetal head measurement method according to one embodiment of the invention.

FIG. 5 shows the next step in the preferred method of the present invention in which the crude boundary of fetal head 50 is filtered to remove outlier points 56. Preferably, two types of filters are used. First, the present invention automatically applies a statistical filter to the crude boundary. The statistical filter removes boundary points with a radial distance more than a predetermined deviation from the mean radius from initial point 52. The amount of deviation represents a tradeoff between how close initial point 52 must be marked to the center of fetal head 50 and the accuracy of the fetal head size measurements. For example, in one embodiment, the predetermined deviation is two standard deviations from the mean radius from initial point 52. A predetermined deviation of two standard deviations permits the user to select initial point 52 close to the center of fetal head 50, as described above. A larger deviation, such as, for example, three standard deviations, permits an even greater flexibility in selecting initial point 52. However, the accuracy of fetal head size measurement may decrease. Conversely, a smaller deviation, such as one standard deviation, results in a more accurate determination of fetal head size. However, initial point 52 must be marked closer to the center of fetal head 50 than if two standard deviations are used.

Second, the present invention preferably applies a symmetric filter for removing all points on the boundary that are not substantially symmetric to each other with respect to initial point 52. The degree of symmetry represents a tradeoff between how close initial point 52 must be marked to the center of fetal head 50 and the accuracy of the fetal head size measurements. In one embodiment, the margin of error in the symmetrical filter is 5 ram. A larger margin of error in degree of symmetry, such as 10 mm, permits the user to select initial point 52 close to the center of fetal head 50, as described above. However, the accuracy of fetal head size measurement may decrease. Conversely, a smaller margin of error in degree of symmetry, such as 2 mm, results in a more accurate determination of fetal head size. However, initial point 52 must be marked closer to the center of fetal head 50.

After filtering the crude boundary to remove outlier points 56 and asymmetric points, the present invention fits a curve 58 through the points of the filtered crude boundary. Curve fitting techniques are well known in the art, and a number of techniques are acceptable. For example, in one embodiment, a cubic spline is fit through the points of the filtered crude boundary. Curve 58 is the initial boundary of fetal head 50 that is input into a first pass of the active contour model.

Modifying the Initial Boundary

Figure 6:
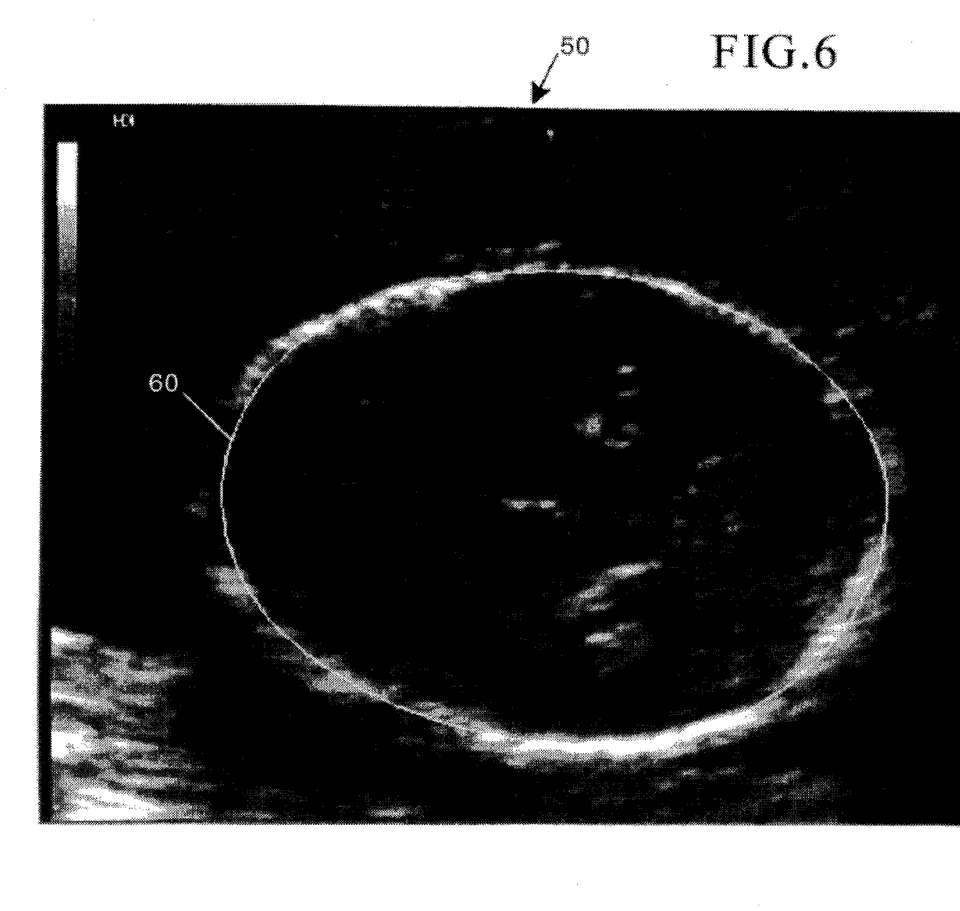
FIG. 6 is an ultrasound display image of a fetal head with an overlaid modified initial boundary at another step of a fetal head measurement method according to one embodiment of the invention.

FIG. 6 shows the next step in the preferred method of the present invention in which the initial boundary is adjusted to derive a boundary which lies between the inner and outer boundaries of the fetal skull. According to the present invention, a first pass of the active contour model is applied to the initial boundary, shown in FIG. 5 as curve 58. The active contour model modifies the initial boundary of curve 58 to yield boundary 60 that closely fits the edges of fetal head 50. The image I used for this first pass of the active contour model is the original image of fetal head 50 filtered with the derivative of a Gaussian with a large standard deviation. This large standard deviation ensures that the contour is attracted to the edges from large distances. However, it merges the inner and outer boundaries of fetal head 50. Therefore, boundary 60 typically does not pass through either the inner boundary or the outer boundary of fetal head 50. Instead, boundary 60 typically passes through the fetal skull between the inner and outer boundaries of fetal head 50.

According to the present invention, active contour model parameters $\alpha$, $\beta$, and $\gamma$ of fetal head 50 are automatically estimated from the initial boundary of curve 58. The contouring process is an iterative process of both estimating model parameters $\alpha$, 62, and $\gamma$, and fitting the initial boundary and ultrasound image data I to the active contour model. Once the iterations achieve less than a threshold improvement over a prior iteration (e.g., when the model parameters $\alpha$, $\beta$, and $\gamma$ and boundary 60 stop changing), the iterative process stops. In one embodiment, the iterative process stops when there is less than an average of 1 pixel improvement for 10 consecutive iterations. The result is an improved boundary estimate that lies between the inner and outer boundaries of fetal head 50. Inner and outer boundaries of fetal head 50 are found next.

Deriving Inner and Outer Boundaries

Figure 7:
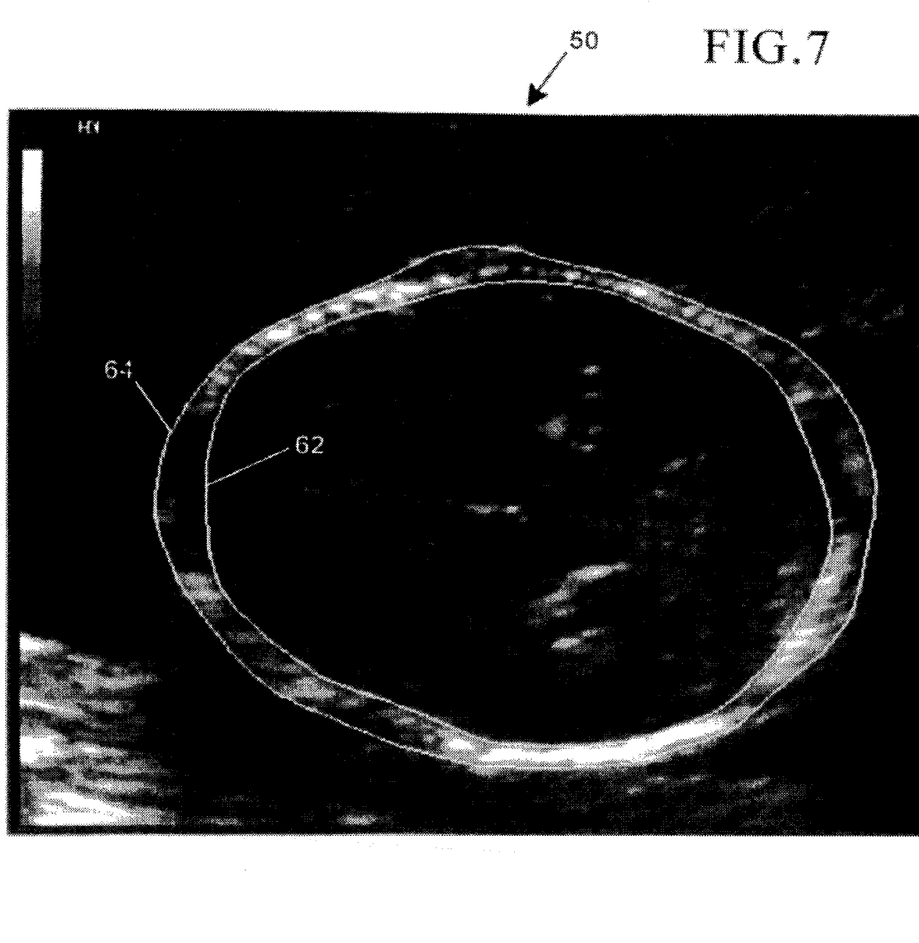
FIG. 7 is an ultrasound display image of a fetal head with overlaid inner and outer fetal head boundaries at another step of a fetal head measurement method according to one embodiment of the invention.

FIG. 7 shows the next step in the preferred embodiment of the method of the present invention in which an inner boundary 62 and an outer boundary 64 of fetal head 50 are found. This step uses an image I filtered with the derivative of a Gaussian with a small standard deviation. The standard deviation used in this step is smaller than the standard deviation of the image filter used in the previous step. The use of a smaller standard deviation prevents the inner and outer edges of fetal head 50 from merging with each other.

Finding inner and outer boundaries 62, 64 of fetal head 50 entails expanding and contracting boundary 60 using expansion and contraction factors. A standard fetal skull thickness is used as both the expansion factor and the contraction factor. Standard fetal skull thickness can vary between 1–3 min. In one embodiment of the invention, a standard fetal skull thickness of approximately 1.2 mm is used.

The present invention performs a second iterative fitting process to find outer boundary 64. Boundary 60 expanded with the expansion factor is input as an initial curve into a second pass of the active contour model. The second pass of the active contour model proceeds in an iterative manner like the first pass of the active contour model; the second pass of the active contour model stops when the model parameters $\alpha$, $\beta$, and $\gamma$ and the outer boundary 64 stop changing.

The present invention then performs a third iterative fitting process to find inner boundary 62. Boundary 60 contracted with the contraction factor is input as an initial curve into a third pass of the active contour model. The third pass of the active contour model proceeds in an iterative manner and stops when the model parameters $\alpha$, $\beta$, and $\gamma$ and the inner boundary 62 stop changing. As seen in FIG. 7, the results of this stage of processing are inner and outer boundaries 62 and 64 of fetal head 50.

Measuring Head Circumference and Biparietal Diameter

Figure 8:
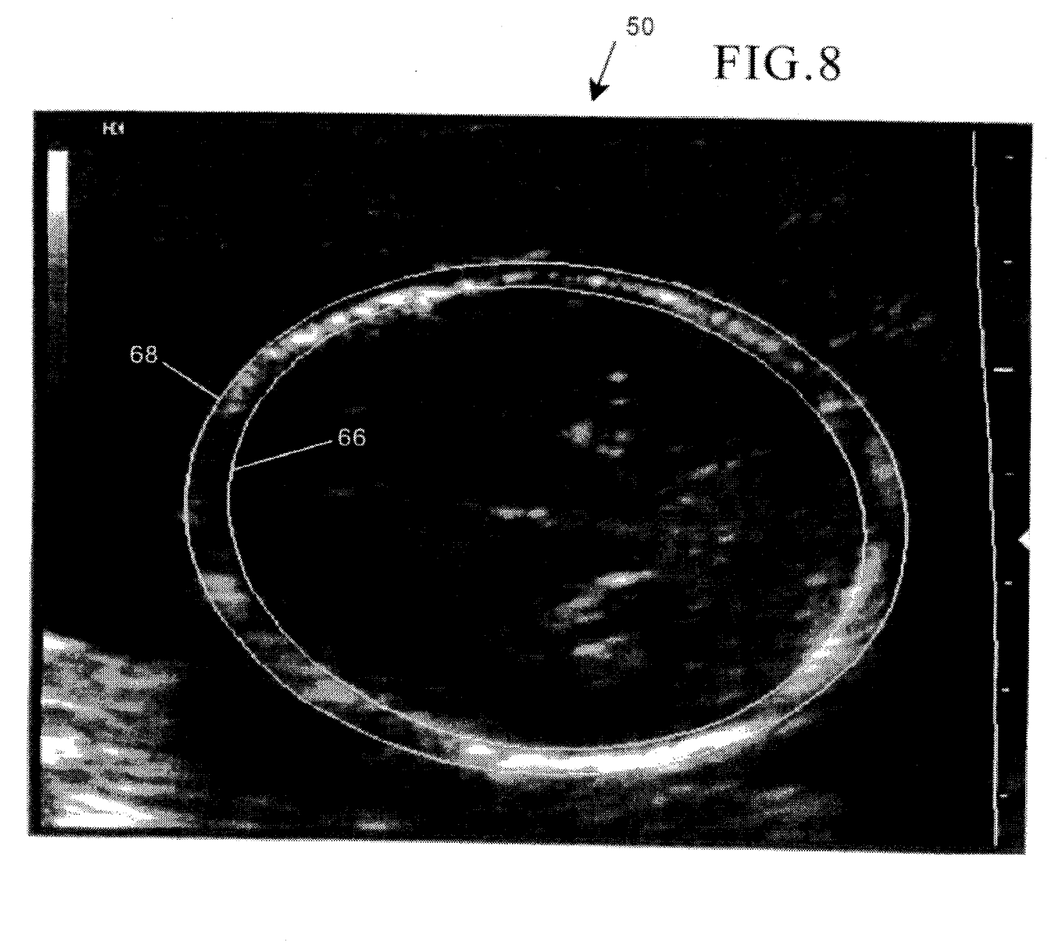
FIG. 8 is an ultrasound display image of a fetal head with overlaid inner and outer ellipses fitted to the inner and outer fetal head boundaries at another step of a fetal head measurement method according to one embodiment of the invention.
Figure 9:
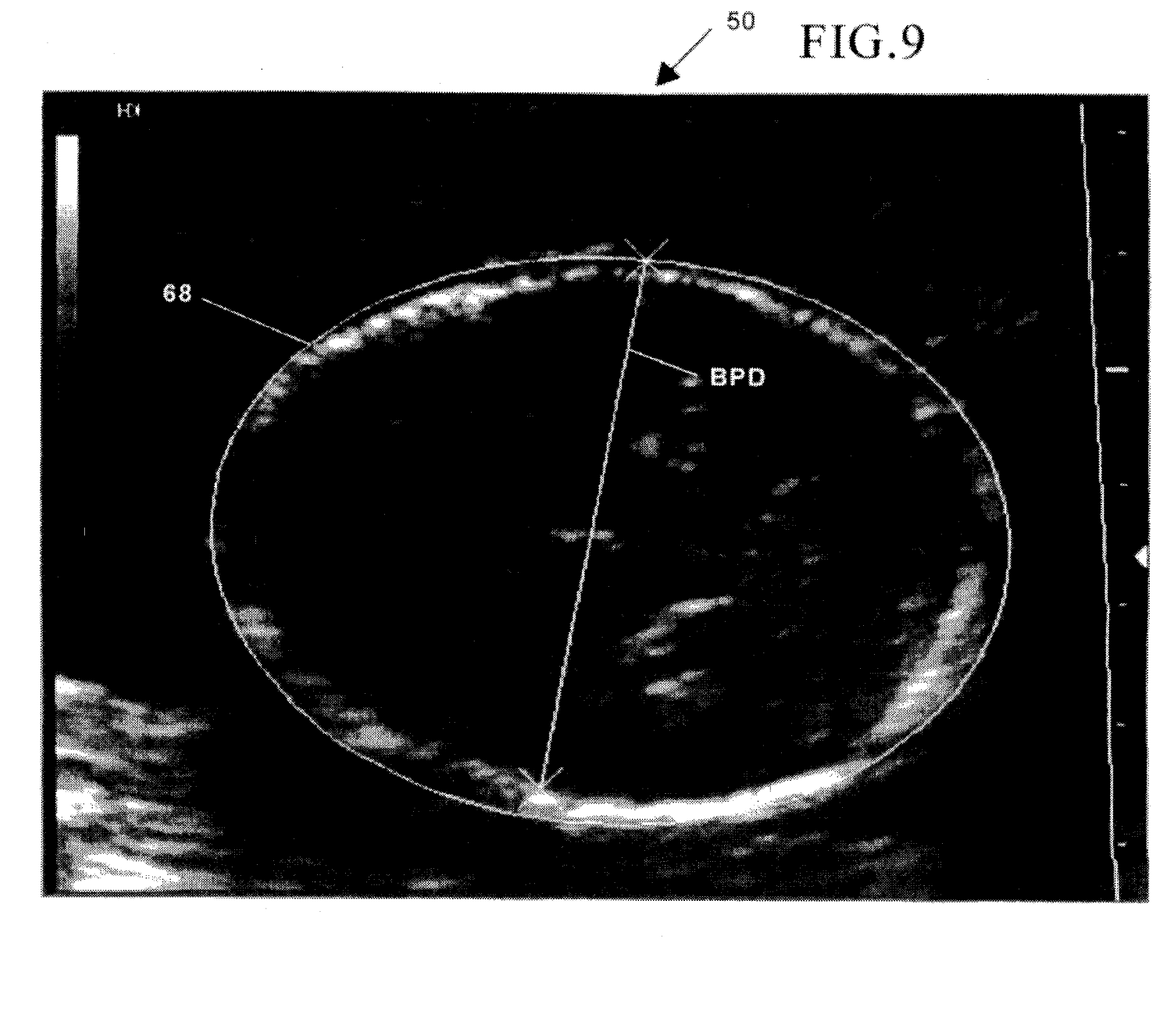
FIG. 9 is an ultrasound display image of a fetal head with overlaid lines indicating head circumference and biparietal diameter.

FIGS. 8 and 9 show the final steps of the method of the preferred embodiment of the present invention in which fetal head size is automatically derived from inner boundary 62 and outer boundary 64. As shown in FIG. 8, inner and outer ellipses 66 and 68 are fit to inner and outer boundaries 62 and 64, respectively. As shown in FIG. 9, head circumference HC for fetal head 50 is the circumference of outer ellipse 68. The circumference HC of outer ellipse 68 is calculated by solving the following equation:

$$HC = 4a \int_{t=0}^{\pi/2} \sqrt{1 - e^2 \sin^2 t}\; dt,$$

where a=distance from the center of fetal head 50 to a major vertex of the major axis of outer ellipse 68;

c=distance from the center of fetal head 50 to a focus of outer ellipse 68; and e=c/a, the eccentricity of outer ellipse 68.

Biparietal diameter BPD, also shown in FIG. 9, is the average length of the minor axes of inner ellipse 66 and outer ellipse 68.

Meritorious Effects and Advantages

One advantage of the method for automatically measuring fetal head size is that the time portion of the diagnostic exam allocated toward fetal head measurement is reduced. A meritorious effect of such time reduction is a decrease in health care costs. Another advantage of the process is reduced interobserver variability. A meritorious effect of such reduction is more reliable data pool for predicting fetal health, size, and age.

Another advantage of the method of the present invention is that a boundary can be detected for a curved object using ultrasound imaging techniques. A meritorious effect of such a boundary detection is that it is not limited to detection of a fetal head boundary. For example, according to the present invention, a boundary can be derived from an ultrasound image of a kidney, a liver, a prostate tumor, ventricles of a pediatric brain, or a fetal femur. As a further example, the number and size of ovarian follicles can be measured. Moreover, cross sectional area and diameter of arteries and veins can be measured from transcutaneous or intravascular ultrasound images. These examples are given as non-limiting examples; a boundary of any curved object can be detected according to the present invention.

Another advantage of the method of the present invention is that a sonographer may be aided in identifying the correct orientation for acquiring a fetal head image. Typically, the fetal head image used for BPD and HC measurements is selected based upon certain landmarks on the image. In addition to identified landmarks, image selection is based upon size of the displayed head. The image plane where BPD is the smallest is typically chosen. Advantageously, the present invention can track BPD measurement of the fetal head as images change. According to the present invention, once a fetal head boundary is detected on an image frame, the boundary can be used as an initial curve for the next image frame. The sonographer does not need to mark an initial point on every sequential image. This allows the method of the present invention to proceed very quickly and give a sonographer timely feedback regarding transducer orientation.

Although a preferred embodiment of the invention has been illustrated and described, various alternatives, modifications and equivalents may be used. For example, the method can be performed by an image processor internal to a medical ultrasound imaging device, or it can be performed by an external signal processor. Further, the present invention can detect a boundary of a curved object other than a fetal head. Therefore, the foregoing description should not be taken as limiting the scope of the inventions which are defined by the appended claims.

What is claimed is:

1. A method for automatically measuring fetal head size based upon ultrasound image data of the fetal head, the method comprising the steps of:

detecting an ultrasound image of the fetal head;

identifying a radial maxima point on each of a plurality of radii extending from a substantially common vertex point within the fetal head image, each radial maxima point corresponding to an ultrasound sample along its corresponding radius and having a maximum ultrasound echo strength;

defining a first curve and a detected boundary from the radial maxima points;

modifying the detected boundary to define an initial fetal head boundary;

deriving an inner fetal head boundary and outer fetal head boundary from the initial fetal head boundary and a predetermined fetal skull thickness; and computing fetal head size from the inner fetal head boundary and outer fetal head boundary.

2. The method of claim 1 wherein said step of detecting an ultrasound image of the fetal head is performed at an orientation selected by an operator.

3. The method of claim 1 wherein said step of identifying a radial maxima point comprises the step of selecting the substantially common vertex point by an operator.

4. The method of claim 1 wherein said step of defining a first curve comprises the step of filtering out radial maxima points farther than a threshold distance from the substantially common vertex point, the threshold distance being based upon an average distance between the substantially common vertex point and the plurality of radial maxima points.

5. The method of claim 4 wherein said step of defining a detected boundary further comprises the steps of filtering out radial maxima points that are asymmetric to other radial maxima points and fitting remaining unfiltered radial maxima points to a second curve, the second curve being the detected curved boundary.

6. The method of claim 1 wherein said step of modifying the detected boundary comprises the step of performing an iterative estimation of the initial fetal head boundary and a first set of active contour model parameters using an active contour model, the iterative estimation stopping when values of the estimated initial fetal head boundary and the estimated active contour model parameters from an iteration are within a predetermined threshold of values of the estimated fetal head boundary and the estimated active contour model parameters from a prior iteration.

7. The method of claim 1 wherein said step of deriving an inner fetal head boundary and outer fetal head boundary comprises the step of performing an iterative estimation of inner and outer fetal head boundaries and second and third sets of active contour model parameters using an active contour model, the iterative estimation stopping when values of the estimated inner and outer fetal head boundaries and the second and third sets of active contour model parameters from an iteration are within a predetermined threshold of values of the estimated inner and outer fetal head boundaries and the second and third sets of active contour model parameters from a prior iteration.

8. The method of claim 1 wherein said step of deriving an inner fetal head boundary and outer fetal head boundary comprises the step of contouring the inner fetal head boundary to an ellipse shape and contouring the outer fetal head boundary to an ellipse shape.

9. The method of claim 1 wherein said step of computing fetal head size comprises the step of computing circumference of the outer fetal head boundary.

10. The method of claim 1 wherein said step of computing fetal head size comprises the step of computing biparietal diameter as an average of the inner fetal head boundary and the outer fetal head boundary.

11. The method of claim 10 wherein the value of biparietal diameter changes with changes in transducer orientation, and said step of detecting an ultrasound image of the fetal head is performed at an orientation selected by an operator such that biparietal diameter has a smallest value.

12. An ultrasound system for automatically measuring fetal head size, the ultrasound system comprising:

a transducer array for transmitting ultrasound energy into a patient in the vicinity of an internal fetus and for receiving echoes of the ultrasound energy, the received echoes being transformed into electronic echo signals;

an image processor for generating ultrasound image data from the received echo signals;

a display device for displaying the ultrasound image data generated by the image processor;

means for identifying a radial maxima point on each of a plurality of radii extending from a substantially common vertex point within a fetal head image, each radial maxima point corresponding to an ultrasound sample along its corresponding radius and having a maximum ultrasound echo strength;

means for defining a first curve and a detected boundary from the radial maxima points;

means for modifying the detected boundary to define an initial fetal head boundary;

means for deriving an inner fetal head boundary and outer fetal head boundary from the initial fetal head boundary and a predetermined fetal skull thickness; and means for computing fetal head size from the inner fetal head boundary and outer fetal head boundary.

13. The ultrasound system of claim 12 wherein said defining means comprises:

first filter means for filtering out radial maxima points farther than a threshold distance from the substantially common vertex point, the threshold distance being based upon an average distance between the substantially common vertex point and the plurality of radial maxima points;

second filter means for filtering out radial maxima points that are asymmetric to other radial maxima points;

means for fitting remaining unfiltered radial maxima points to a second curve, the second curve being the detected curved boundary; and means for fitting remaining unfiltered radial maxima points to a second curve, the second curve being the detected curved boundary.

14. The ultrasound system of claim 12 wherein said deriving means comprises means for applying an active contour model.

15. A method for automatically detecting a curved boundary within an ultrasound image of an object, the image data being formed by scanning the object with an ultrasound transducer to achieve image data, the detected boundary substantially corresponding to a physical boundary of the object, the method comprising the steps of:

testing the image data to identify a plurality of radial maxima points relative to a substantially common vertex point of the object, each of the plurality of radial maxima points being a point along a radial line extending from the vertex point and corresponding to a maximum ultrasound echo strength;

filtering out radial maxima points farther than a threshold distance from the vertex point, the threshold distance being based upon an average distance between the vertex point and the plurality of radial maxima points;

filtering out radial maxima points that are asymmetric to other radial maxima points; and fitting remaining unfiltered radial maxima points to a curve, the curve being the detected curved boundary.

16. The method of claim 15 wherein said step of testing the image data comprises the step of detecting an initial point by an operator using ultrasound imaging, the initial point being the substantially common vertex point.

17. The method of claim 15 wherein at least 100 radial maxima points are identified.

18. The method of claim 15 wherein the threshold distance is two standard deviations from a mean radius from the substantially common vertex point.

19. The method of claim 15, further comprising the step of modifying the detected curved boundary to define an initial curved boundary, the initial curved boundary corresponding to the physical boundary of the object.

20. The method of claim 19 wherein said step of modifying the detected curved boundary comprises the step of performing an iterative estimation of the initial curved boundary and a fourth set of active contour model parameters using an active contour model, the iterative estimation stopping when values of the estimated initial curved boundary and the fourth set of active contour model parameters from an iteration are within a predetermined threshold of values of the estimated initial curved boundary and the fourth set of active contour model parameters from a prior iteration.

* * * * *